(12) United States Patent
Nam et al.

(10) Patent No.: US 9,855,243 B2
(45) Date of Patent: *Jan. 2, 2018

(54) TOPICAL ANTI-INFLAMMATORY PHARMACEUTICAL COMPOSITION WITH ZILEUTON CREAM FORMULATION

(71) Applicant: Qurient Co., Ltd., Seongnam-si, Gyeonggi-do (KR)

(72) Inventors: Ki Yean Nam, Seongnam-si (KR); Jeong Jun Kim, Seoul (KR); Sae Yeon Lee, Yongin-si (KR); Ji Ye Ahn, Seongnam-si (KR); Chunwon Jung, Yongin-si (KR); Jaeseung Kim, Seoul (KR); Hwan Kyu Kang, Ansan-si (KR); Hana Kim, Suwon-si (KR)

(73) Assignee: QURIENT CO., LTD., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/215,909

(22) Filed: Jul. 21, 2016

(65) Prior Publication Data

US 2016/0324827 A1 Nov. 10, 2016

Related U.S. Application Data

(63) Continuation-in-part of application No. 14/777,183, filed as application No. PCT/KR2014/007525 on Aug. 13, 2014.

(30) Foreign Application Priority Data

Oct. 30, 2013 (KR) .......................... 10-2013-0130165

(51) Int. Cl.
| | | |
|---|---|---|
| *A61K 31/381* | (2006.01) | |
| *A61K 9/14* | (2006.01) | |
| *A61K 47/10* | (2017.01) | |
| *A61K 47/06* | (2006.01) | |
| *A61K 9/06* | (2006.01) | |
| *A61K 47/24* | (2006.01) | |
| *A61K 47/44* | (2017.01) | |
| *A61K 9/00* | (2006.01) | |

(52) U.S. Cl.
CPC .......... *A61K 31/381* (2013.01); *A61K 9/0014* (2013.01); *A61K 9/06* (2013.01); *A61K 47/06* (2013.01); *A61K 47/10* (2013.01); *A61K 47/24* (2013.01); *A61K 47/44* (2013.01)

(58) Field of Classification Search
CPC ...... A61K 31/381; A61K 47/06; A61K 47/10; A61K 47/24; A61K 47/44; A61K 9/0014; A61K 9/06

See application file for complete search history.

(56) References Cited

U.S. PATENT DOCUMENTS

| | | |
|---|---|---|
| 8,003,684 B2 | 8/2011 | Hanko |
| 2004/0171599 A1 | 9/2004 | Ledergerber |

FOREIGN PATENT DOCUMENTS

| | | |
|---|---|---|
| KR | 10-2004-0008166 | 1/2004 |
| WO | WO 2008/106081 | 9/2008 |
| WO | WO 2013/056994 A1 | 4/2013 |

*Primary Examiner* — Sreeni Padmanabhan
*Assistant Examiner* — Jody Karol
(74) *Attorney, Agent, or Firm* — Saliwanchik, Lloyd & Eisenschenk

(57) ABSTRACT

Provided herein is a zileuton cream type topical anti-inflammatory pharmaceutical composition, and more particularly, a zileuton cream type topical anti-inflammatory pharmaceutical composition capable of retaining stability at room temperature and of being applied topically to maximize medical effects while minimizing absorption to an entirety of body, thereby minimizing toxicity caused by the compound so as to be suitable to topical treatment of skin diseases caused by leukotriene.

11 Claims, 3 Drawing Sheets

| Plasma Concentration of Cream 1(Q301) after TP at 20 mg/cm² (ng/mL) | | | | | | | |
|---|---|---|---|---|---|---|---|
| Time (h) | Concentration for animal (ng/mL) | | | | | | Mean (ng/mL) |
| | P1 | P2 | P3 | P4 | P5 | P6 | |
| -0.50 | BQL | BQL | BQL | BQL | BQL | BQL | ND |
| 0.25 | BQL | 6.14 | BQL | -- | -- | -- | ND |
| 0.50 | -- | -- | -- | BQL | BQL | BQL | ND |
| 1.00 | BQL | BQL | BQL | -- | -- | -- | ND |
| 1.50 | -- | -- | -- | BQL | BQL | BQL | ND |
| 2.00 | -- | -- | -- | BQL | BQL | BQL | ND |
| 3.00 | -- | -- | -- | BQL | BQL | BQL | ND |
| 4.00 | -- | -- | -- | BQL | BQL | BQL | ND |
| 6.00 | -- | -- | -- | BQL | BQL | BQL | ND |
| 8.00 | -- | -- | -- | BQL | BQL | BQL | ND |

FIG. 5

TOPICAL ANTI-INFLAMMATORY PHARMACEUTICAL COMPOSITION WITH ZILEUTON CREAM FORMULATION

CROSS-REFERENCE TO RELATED APPLICATIONS

This application is a continuation-in-part of U.S. patent application Ser. No. 14/777,183, filed on Sep. 15, 2015, which is a National Stage application of International Application Number PCT/KR2014/007525, filed Aug. 13, 2014; which claims priority to Korean Patent Application No. 10-2013-0130165, filed Oct. 30, 2013; all of which are incorporated herein by reference in their entirety.

FIELD OF THE INVENTION

The present invention relate to a topical pharmaceutical composition with zileuton cream formulation for treatment of skin diseases caused by leukotriene.

BACKGROUND

Leukotriene is a metabolite of arachidonic acid, and is well known as an inflammatory factor that is deeply involved in causing inflammation, edema, and secretion of mucus and the like. A well-known leukotriene inhibitor developed so far is zileuton ((±)-1-(1-(benzo [b]thiophen-2-yl)ethyl)-1-hydroxyurea).

Zileuton is a mixture of stereoisomers: (R)-1-(1-(benzo [b]thiopen-2-yl)ethyl)-1-hydroxyure and (S)-1-(1-(benzo[b] thiophen-2-yl)ethyl)-1-hydroxyurea. It has been approved as an oral drug for treatment of asthma, and is known to be administrable twice a day. Clinical trials have shown that zileuton exhibits an effective anti-inflammatory pharmaceutical effect against inflammation reaction of asthma.

Clinical trials have revealed that oral administration of zileuton alleviates atopic dermatitis symptoms. However, zileuton is not being widely used despite its excellent anti-inflammatory effects due to toxicity of the compound.

Zileuton has significant hepatotoxicity, and thus an oral administration of zileuton should be accompanied by monitoring of liver functions of the patient.

BRIEF SUMMARY

Therefore, a purpose of the present invention is to provide a topical pharmaceutical composition with a cream formulation, capable of applying zileuton topically to skin lesions of diseases caused by topical skin inflammation reactions such as atopic dermatitis, acne, various types of urticaria, psoriasis, eczema, bullous skin diseases such as bullous pemphigoid, collagenoses, Sjogren-Larsson syndrome, mastocytosis and the like, and maximizing pharmaceutical effects of zileuton while minimizing absorption to an entirety of a patient's body so as to minimize toxicity of the compound.

Another purpose of the present invention is to provide a cream type topical pharmaceutical composition having improved physiochemical stability.

Further, another purpose of the present invention is to provide a method for preparing a topical pharmaceutical composition with zileuton cream formulation.

Further, still another purpose of the present invention is to provide a method for relieving or treating atopic dermatitis, acne, urticaria, psoriasis, eczema, a bullous skin disease, collagenoses, Sjogren-Larsson syndrome, or acne in skin lesions of mastocytosis using the pharmaceutical composition.

In order to achieve the purposes, one embodiment of the present invention provides a cream type topical pharmaceutical composition, comprising zileuton, an aqueous solvent, an organic solvent, a thickening agent, and an emulsifier.

The aqueous solvent may comprise water or a pH buffer solution, and the organic solvent may comprise, without any limitation, at least one selected from the group consisting of ethanol, polyethylene glycol, hexylene glycol, propylene glycol monocaprylate, benzyl alcohol, N-methyl pyrrolidone, triacetin, isopropyl myristate, propylene glycol dicaprylocaprate, medium chain triglycerides, castor oil, olive oil, safflower oil, light mineral oil, squalane, dimethicone, cyclomethicone, polyglyceryl-6 dioleate, polyglyceryl-10 monooleate, polyglyceryl-10 dioleate, polyoxyl 40 hydrogenated castor oil, caprylocaproyl polyoxyl-8 glycerides, polyoxyethylene (20) sorbitan monolaurate, diethylene glycol monoethyl ether, and dimethyl sulfoxide.

The aqueous solvent may be a pH buffer solution having a pH of about 4 to about 5.

The thickening agent may comprise at least one of white petrolatum and white wax.

The emulsifier may comprise at least one selected from a group consisting of phospholipid, stearyl alcohol and propylene glycol stearate. Preferably, the emulsifier may comprise phospholipids including hydrogenated lecithin.

Furthermore, the pharmaceutical composition of the present invention may further comprise a preservative.

The preservative may comprise at least one selected from a group consisting of methylparaben, ethylparaben, propylparaben, isobutylparaben, butyl paraben, 2-phenoxy ethanol, and 4-hydroxybenzoic acid.

The pharmaceutical composition of the present invention may comprise zileuton of about 0.05 to about 2 weight % as an active pharmaceutical ingredient; water or pH buffer solution of about 30 to about 34 weight %; white petrolatum of about 36 to about 40 weight %; white wax of about 4 to about 8 weight %; propylene glycol of about 16 to about 22 weight %; phospholipid of about 2 to about 6 weight %; and preservative of about 0.005 to about 0.04 weight %.

Further, the composition may comprise zileuton of about 0.1 to about 1 weight %; water or pH buffer solution of about 31 to about 33 weight %; white petrolatum of about 37 to about 39 weight %; white wax of about 5 to about 7 weight %; propylene glycol of about 18 to about 20 weight %; phospholipid of about 3 to about 5 weight %; and preservative of about 0.01 to about 0.03 weight %.

The composition may be for topical application to human skin, and the zileuton may be racemic zileuton.

Another embodiment of the present invention provides a method for relieving or treating atopic dermatitis, acne, urticaria, psoriasis, eczema, a bullous skin disease, collagenoses, Sjogren-Larsson syndrome, or acne in skin lesions of mastocytosis, comprising administering, to a subject in need of such relief or treatment, the composition of the present invention.

Still another embodiment of the present invention provides a method for preparing a cream type topical anti-inflammatory pharmaceutical composition, including mixing zileuton, an aqueous solvent, an organic solvent, a thickening agent, an emulsifier, and optionally a preservative under a mixing condition of a temperature of about 30 to about 80° C. and about 600 to about 1200 rpm, for about 10 to about 60 minutes.

In the method, the aqueous solvent may be water or pH buffer solution having a pH of about 4 to about 5.

The method may further include cooling the mixed ingredients at a temperature of about 20 and about 30° C. while stirring at about 600 rpm or less.

As aforementioned, the present invention provide a cream type topical pharmaceutical composition that comprises zileuton as an active pharmaceutical ingredient and exhibits treatment effects to diseases caused by topical skin inflammation reactions such as atopic dermatitis, acne, various types of urticaria, psoriasis, eczema, bullous skin diseases such as bullous pemphigoid, collagenoses, Sjogren-Larsson syndrome, skin lesions of mastocytosis, and the like.

Furthermore, the cream type pharmaceutical composition according to the present invention has a pharmacokinetic profile that enables zileuton that is a leukotriene inhibitor to be absorbed to skin effectively but minimizing the amount of absorption to an entirety of a patient's body, and a physiochemical stability.

BRIEF DESCRIPTION OF THE DRAWINGS

FIGS. 4 and 5 show research results of the pharmacokinetic profile of the pharmaceutical composition according to the present invention in a minipig.

DETAILED DESCRIPTION

Figure 1:
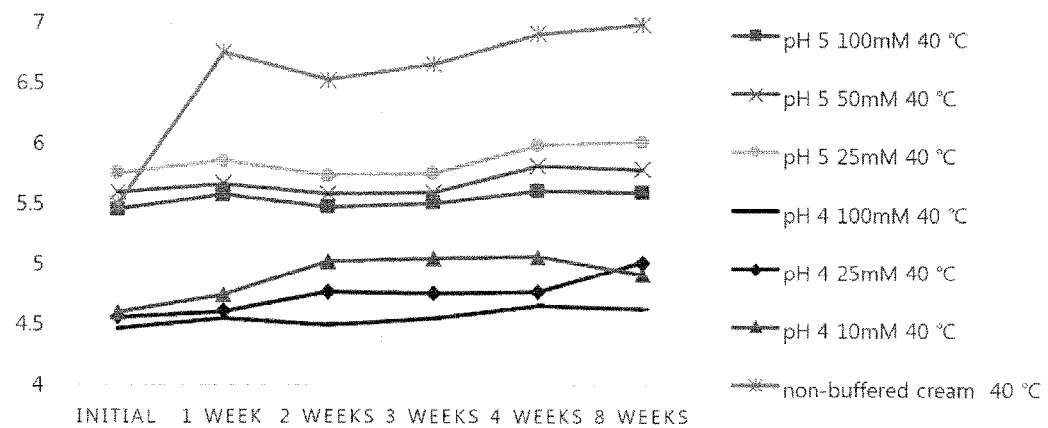
FIG. 1 is a graph showing the pH changes of the pharmaceutical compositions with or without a pH buffer solution at 40° C. over 4 weeks.

The present invention now will be described more fully hereinafter in the following detailed description of the invention, in which some, but not all embodiments of the invention are described. Indeed, the present invention may be embodied in many different forms and should not be construed as limited to the embodiments set forth herein; rather, these embodiments are provided so that this disclosure will satisfy applicable legal requirements.

The following detailed description is provided to assist the reader in gaining a comprehensive understanding of the compositions and methods described herein. Accordingly, various changes, modifications, and equivalents of the compositions and/or methods described herein will be suggested to those of ordinary skill in the art. Also, descriptions of well-known functions and constructions may be omitted for increased clarity and conciseness.

Furthermore, a singular form may include a plural from as long as it is not specifically mentioned in a sentence. Furthermore, "comprise/includes" or "comprising/including" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

Herein below, explanation will be made on a pharmaceutical composition according to the present invention, a method for preparing the same, and a use thereof.

In order to provide a cream type topical formulation comprising zileuton as an active pharmaceutical ingredient, which exhibits effective treatment effects to atopic dermatitis and acne and the like, the inventors of the present invention sought for ingredients that can be applied with zileuton among the ingredients being used in cream type formulations, and sought for amount ratio of the ingredients for preparing a cream formulation comprising them, and then defined optimal concentration of the zileuton and stabilization conditions for realizing physiochemical stability, and thereby completed the present invention.

Therefore, the present invention provides a cream type topical pharmaceutical composition comprising zileuton, an aqueous solvent, an organic solvent, a thickening agent and an emulsifier.

Herein, zileuton is a mixture of stereoisomer: (R)-1-(1-(benzo[b]thiopen-2-yl)ethyl)-1-hydroxyure and (S)-1-(1-(benzo[b]thiophen-2-yl)ethyl)-1-hydroxyurea, in a white powder form, and may be racemic zileuton. That is, the present invention provides a cream type composition optimized to racemic zileuton as an active pharmaceutical ingredient.

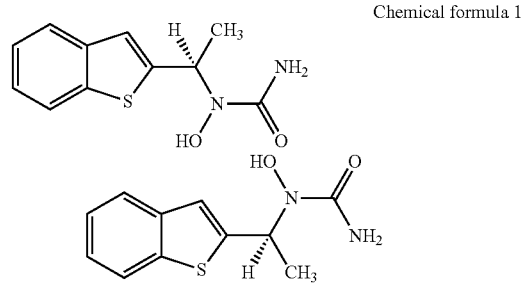

Chemical formula 1

The zileuton may be synthesized chemically, or is available commercially (Cornerstone Therapeutics Inc., product name: ZYFLO, ZYFLO CR etc.)

The aqueous solvent used in the pharmaceutical composition of the present invention may comprise water or a pH buffer solution.

In a preferred embodiment of the present invention, the aqueous solvent is a pH buffer solution. In a more preferred embodiment, the aqueous solvent may be a pH buffer solution having a pH of about 4 to about 5. For example, the pH buffer solution may be, but not limited to, citrate buffer (citric acid with sodium citrate), acetate buffer (acetic acid with sodium acetate) or phthalate buffer (potassium hydrogen phthalate with sodium hydroxide or formaldehyde).

In case of using such pH buffer solution as an aqueous solution, the pharmaceutical composition of the present invention may exhibit more improved chemical stability. This is because the pH buffer solution controls the pH change of the composition so that any possible hydrolysis of zileuton to produce hydrolytic degradants which are undesirable impurities in the composition can be prevented, and thereby the chemical stability of the composition can be improved.

In a preferred embodiment of the present invention, the production of hydrolytic degradants of zileuton can be minimized by stabilizing the pH of the composition by using a pH buffer solution, and thereby the chemical stability of the composition may be improved.

The organic solvent used in the pharmaceutical composition of the present invention may comprise, but not limited to, at least one selected from the group consisting of ethanol, polyethylene glycol, hexylene glycol, propylene glycol monocaprylate, benzyl alcohol, N-methyl pyrrolidone, triacetin, isopropyl myristate, propylene glycol dicaprylocaprate, medium chain triglycerides, castor oil, olive oil, safflower oil, light mineral oil, squalane, dimethicone, cyclomethicone, polyglyceryl-6 dioleate, polyglyceryl-10 monooleate, polyglyceryl-10 dioleate, polyoxyl 40 hydrogenated castor oil, caprylocaproyl polyoxyl-8 glycerides, polyoxyethylene (20) sorbitan monolaurate, diethylene glycol monoethyl ether, and dimethyl sulfoxide.

In a preferred embodiment of the present invention, the organic solvent is propylene glycol.

The thickening agent used in the pharmaceutical composition of the present invention may comprise, but not limited to, at least one of white petrolatum and white wax.

The emulsifier may be, but not limited to, at least one selected from a group consisting of hydrogenated lecithin, stearyl alcohol and propylene glycol stearate. Preferably, the emulsifier may comprise phospholipids including hydrogenated lecithin. For example, the emulsifier is commercially available as a product name of Phospholipon 90H.

The pharmaceutical composition of the present invention may further comprise a preservative.

The preservative may be, but not limited to, at least one selected from a group consisting of methylparaben, ethylparaben, propylparaben, isobutylparaben, butyl paraben, 2-phenoxy ethanol, and 4-hydroxybenzoic acid.

The pH buffer solution, organic solvent, thickening agent such as white petrolatum and white wax, emulsifier, and preservative to be used in the pharmaceutical composition of the present invention are available commercially.

In one exemplary embodiment, the cream type pharmaceutical composition of the present invention may comprise zileuton of about 0.05 to about 2 weight % as an active pharmaceutical ingredient; water or pH buffer solution of about 30 to about 34 weight %; white petrolatum of about 36 to about 40 weight %; white wax of about 4 to about 8 weight %; propylene glycol of about 16 to about 22 weight %; phospholipid of about 2 to about 6 weight %; and preservative of about 0.005 to about 0.04 weight %.

In another exemplary embodiment, the cream type pharmaceutical composition of the present invention may comprise zileuton of about 0.1 to about 1 weight %; water or pH buffer solution of about 31 to about 33 weight %; white petrolatum of about 37 to about 39 weight %; white wax of about 5 to about 7 weight %; propylene glycol of about 18 to about 20 weight %; phospholipid of about 3 to about 5 weight %; and preservative of about 0.01 to about 0.03 weight %.

The cream type topical pharmaceutical composition of the present invention may retain its physical and chemical stability for about 4 weeks or more under the temperature condition of about 25 to about 40° C.

The present invention also provides a method for relieving or treating atopic dermatitis, acne, urticaria, psoriasis, eczema, a bullous skin disease, collagenoses, Sjogren-Larsson syndrome, or acne in skin lesions of mastocytosis, wherein said method comprises administering, to a subject in need of such relief or treatment, a composition of the present invention.

In the method for relieving or treating any of the aforementioned diseases according to the present invention, the composition may be applied topically to human skin.

According to an embodiment of the present invention, the medical effect of the cream type topical pharmaceutical composition has been verified in a Delayed Type Hypersensitivity Reaction in mouse induced by DNFB. The test article was applied to a mouse's skin 3 times a day, and then the medical effect was measured. Furthermore, an excess amount of the zileuton was injected using a non-optimized test vehicle, acetone. Test results showed that an increase of thickness of the mouse's ear caused by inflammation and edema in the mouse model administered with the cream type pharmaceutical composition of the present invention was effectively inhibited, proving that the composition has an effective anti-inflammation function.

In order to determine whether or not a medical effect caused by absorption to an entirety of body is included, absorption to skin and body absorption pattern were evaluated. For this purpose, a skin PK was examined from a minipig having a skin structure most similar to human. Test results showed effective skin absorption patterns, but showed no systemic exposure pattern. That is, it was identified that a cream type topical pharmaceutical composition according to the present invention effectively induces skin absorption, and minimizes body absorption, proving that the composition according to the present invention is suitable formulation for administration to human skin.

Therefore, a cream type topical pharmaceutical composition according to the present invention exhibits an anti-inflammatory effect by inhibiting formation of leukotriene, and thus is effective in relieving or treating diseases caused by topical skin inflammation reaction such as atopic dermatitis, acne, various types of urticaria, psoriasis, eczema, bullous skin diseases such as bullous pemphigoid, collagenoses, Sjogren-Larsson syndrome, skin lesions of mastocytosis, and the like.

The acne may be an inflammatory acne selected from a group consisting of acne papulosa, acne pustulosa, acne papulopustolosa, and severe inflammatory acne.

The cream type pharmaceutical composition may be for topical application to human skin. More specifically, it may be applied topically once to four times a day.

Further, the present invention also provides a preparation method for a cream type topical pharmaceutical composition, the method comprising mixing zileuton, an aqueous solvent, an organic solvent, a thickening agent, and emulsifier under a mixing condition of a temperature of 30 and 80° C. and 600 to 1200 rpm.

The mixing may be performed for 10 to 60 minutes.

The aqueous solvent used in the method may comprise a pH buffer solution. In a preferred embodiment, the aqueous solvent may be, a pH buffer solution having a pH of about 4 to about 5. For example, the pH buffer solution may be, but not limited to, citrate buffer (citric acid with sodium citrate), acetate buffer (acetic acid with sodium acetate) or phthalate buffer (potassium hydrogen phthalate with sodium hydroxide or formaldehyde).

In the mixing step, a preservative may be further mixed.

In one exemplary embodiment, the preparation method for a cream type topical pharmaceutical composition of the present invention may comprise mixing zileuton of about 0.05 to about 2 weight %; water or pH buffer solution of about 30 to about 34 weight %; white petrolatum of about 36 to about 40 weight %; white wax of about 4 to about 8 weight %; propylene glycol of about 16 to about 22 weight %; phospholipid of about 2 to about 6 weight %; and preservative of about 0.005 to about 0.04 weight %.

HPMC F4M, carbomer (carbopol 940), propylene glycol stearate, and aluminum starch octenylsuccinate were found to be suitable, whereas Ceteareth-20 was found to be unsuitable.

TABLE 1

| No. | Excipient | API: Excipient ratio | Day 0 Appearance | Day 0 Recovery % | Day 0 TRS. % | 2 weeks, 50° C. Appearance | 2 weeks, 50° C. Recovery % | 2 weeks, 50° C. TRS. % | 4 weeks, 50° C. Appearance | 4 weeks, 50° C. Recovery % | 4 weeks, 50° C. TRS. % |
|---|---|---|---|---|---|---|---|---|---|---|---|
| 1 | Zileuton | API | — | — | 2.378 | White powder | 101.47 101.30 | 3.311 3.006 | White powder | 99.12 98.23 | 2.711 2.493 |
| 2 | Stearyl alcohol | 1:1 | White powder | 98.71 | 3.311 | White powder | 101.69 101.28 | 2.935 2.796 | White powder | 102.91 98.77 | 2.512 2.567 |
| 3 | Ceteareth-20 | 1:1 | White powder | 100.34 | 2.394 | White power | 99.99 100.36 | 3.445 3.365 | White semisolid | 97.59 96.39 | 3.632 3.549 |
| 4 | Phospholipon 90H | 1:1 | White powder | 100.61 | 2.400 | White powder | 101.50 102.21 | 2.820 2.846 | White powder | 97.26 103.30 | 2.557 2.429 |
| 5 | White wax | 1:1 | White powder | 99.46 | 2.372 | White powder | 100.70 102.20 | 2.863 2.843 | White powder | 98.77 97.31 | 2.459 2.381 |
| 6 | Titanium dioxide | 1:1 | White powder | 100.59 | 2.344 | White powder | 102.55 102.86 | 2.803 2.839 | White powder | 99.14 99.17 | 2.507 2.504 |
| 7 | Hypromellose (HPMC) | 1:1 | White powder | 103.72 | 2.610 | White powder | 102.67 102.97 | 2.864 2.949 | White powder | 98.86 100.86 | 2.555 2.580 |
| 8 | Carbomer | 1:1 | White powder | 99.34 | 3.326 | White powder | 102.45 103.39 | 2.385 3.067 | White powder | 99.63 97.65 | 2.330 2.403 |

In another exemplary embodiment, the preparation method for a cream type topical pharmaceutical composition of the present invention may comprise mixing zileuton of about 0.1 to about 1 weight %; water or pH buffer solution of about 31 to about 33 weight %; white petrolatum of about 37 to about 39 weight %; white wax of about 5 to about 7 weight %; propylene glycol of about 18 to about 20 weight %; phospholipid of about 3 to about 5 weight %; and preservative of about 0.01 to about 0.03 weight %.

The preparation method for a cream type topical pharmaceutical composition may further comprise cooling the resultant from the mixing under the condition of a temperature of about 20 and about 30° C. while stirring at about 600 rpm or less.

The cream type topical pharmaceutical composition prepared through the aforementioned method may retain its stability for about 4 weeks or more at a temperature of about 25 to about 40° C., and may thus be suitable to topical application.

Hereinafter, examples of a cream type topical pharmaceutical composition of the present invention will be explained. However, the examples are intended for just illustrating, but not limiting the scope of the present invention thereto.

Example 1

Preparing Zileuton Cream Type Composition

1. Screening Test for Suitability of the Cream Type Composition

Suitability of components generally used in cream formulation with respect to zieluton was screened, prior to preparing a zieluton cream formulation. For this purpose, 5 mg of zileuton was dissolved in 5 mg of excipient, and then changes of TRS % (Total Related Substances) were observed for up to 4 weeks under a 50° C. condition. That is, the stability of excipient at 50° C. was tested.

As a result, as illustrated in Table 1 shown below, stearyl alcohol, phospholipon 90H, white wax, titanium dioxide, In the solution stability test, suitability with solvents for solubilizing zileuton (ethanol, PEG400, propylene glycol, hexylene glycol, capryol 90, benzyl alcohol, water) was screened. For this purpose, 10 mg of zileuton was dissolved in a 2 mL vehicle (solvent), and then changes of TRS % were observed in conditions of 25° C., 40° C., and 70° C., respectively.

As a result, as illustrated in Tables 2 and 3 below, most of the solvents were suitable to zileuton under the 25° C. condition, but were unstable under the condition of 40° C. or 70° C. Table 2 shows the result of stability test of the solution at 25° C., and Table 3 shows the result of stability test of the solution at 40° C. or 70° C.

TABLE 2

| Solvents | Temp. | TRS (%) Day 0 | TRS (%) Day 1 | TRS (%) Day 3 | TRS (%) Day 8 | TRS increase rate % |
|---|---|---|---|---|---|---|
| Ethanol | 25° C. | 1.255 | 1.014 | 1.951 | 2.137 | 0.882 |
| Polyethylene glycol (PEG-400) | 25° C. | 1.427 | 1.491 | 2.897 | 4.065 | 2.638 |
| Propylene glycol | 25° C. | 1.457 | 1.624 | 1.478 | 2.132 | 0.675 |
| Hexylene glycol | 25° C. | 1.505 | 1.448 | 1.583 | 1.980 | 0.475 |
| Capryol 90 | 25° C. | 1.623 | 1.444 | 1.478 | 2.201 | 0.578 |
| Benzyl alcohol | 25° C. | 1.642 | 0.869 | 1.806 | 2.023 | 0.381 |
| Water | 25° C. | 1.424 | 1.879 | 1.816 | 1.965 | 0.541 |

TABLE 3

| Solvents | Temp. | TRS (%) Day 0 | TRS (%) Day 1 | TRS (%) Day 3 | TRS (%) Day 8 | TRS increase rate % |
|---|---|---|---|---|---|---|
| Ethanol | 40° C. | 1.255 | 1.778 | 2.375 | 4.704 | 3.449 |
| Polyethylene glycol (PEG-400) | 70° C. | 1.427 | 43.725 | 94.366 | 97.142 | 95.715 |
| Propylene glycol | 70° C. | 1.457 | 26.382 | 82.228 | 96.325 | 94.868 |
| Hexylene glycol | 70° C. | 1.505 | 8.061 | 29.999 | 60.352 | 58.847 |
| Capryol 90 | 70° C. | 1.623 | 10.312 | 39.603 | 76.445 | 74.822 |

TABLE 3-continued

| Solvents | Temp. | Day 0 | Day 1 | Day 3 | Day 8 | TRS increase rate % |
|---|---|---|---|---|---|---|
| Benzyl alcohol | 70° C. | 1.642 | 11.350 | 20.397 | 24.250 | 22.608 |
| Water | 70° C. | 1.424 | 35.171 | 80.268 | 91.994 | 90.570 |

Furthermore, the suitability of other various solvents for solubilizing zileuton was screened. For this purpose, solubility of zileuton in each solvent was observed in condition of 25° C.(RT), respectively.

As a result, as illustrated in Table 4 below, all of the solvents listed in Table 4 can be used for solubilize zileuton in manufacturing a zileuton cream formulation. Especially, hydrophilics solvents such as alcohols may be preferably used.

TABLE 4

| Solvent | Zileuton Solubility at RT (% w/w) |
|---|---|
| Triacetin | 0.50-0.72 |
| Isopropyl Myristate | <0.20 |
| Propylene Glycol Dicaprylocaprate | <0.20 |
| Medium Chain Triglycerides | <0.21 |
| Castor Oil | <0.16 |
| Olive Oil | <0.07 |
| Safflower Oil | <0.07 |
| Light Mineral Oil | <0.04 |
| Squalane | <0.04 |
| Dimethicone | <0.06 |
| Cyclomethicone | <0.06 |
| Polyglyceryl-6 Dioleate | <0.06 |
| Polyglyceryl-10 Mono/Dioleate/Caprol PGE-860 | <0.16 |
| Polyoxyl 40 Hydrogenated Castor Oil/Kolliphor RH40 | <0.37 |
| Caprylocaproyl Polyoxyl-8 Glycerides/Labrasol | 10.81-11.42 |
| Polyoxyethylene (20) Sorbitan Monolaurate/Tween 20 | 8.42-9.24 |
| Diethylene Glycol Monoethyl Ether/Transcutol P | 17.11-17.62 |

2. Composition Optimization Test

The components determined as being suitable in the aforementioned suitability screen test were combined, and amount ratios of solvents and ingredients stable under an acceleration condition (30° C., 40° C.) were screened.

For this purpose, by mixing the ingredients other than solvents such as propylene glycol and water and the like under 70° C. according to the amount ratios disclosed in Table 5, and then adding and mixing the remaining solvents while stirring for 30 minutes under a condition of 70° C. and 800 rpm or less. The mixed composition was stirred at 100 rpm or less, and cooled to room temperature. That is, Table 5 below shows results of the test regarding optimized ingredient ratios.

TABLE 5

| Ingredients (wt %) | 2-1 | 2-2 | 2-3 | 2-4 | 2-5 | 2-6 | 2-7 | 2-8 | 2-9 | 2-10 | 2-11 | 2-12 |
|---|---|---|---|---|---|---|---|---|---|---|---|---|
| Zileuton | — | — | — | — | — | — | — | — | — | — | — | — |
| Water | — | — | — | 57 | 16 | — | — | | | 10~31 | | |
| White petrolatum | 43 | 38~48 | | 24 | 20 | 43 | 38 | | | 18~31 | | |
| White wax | 6 | 6 | 6 | 6 | 5 | 7 | 7 | | | 5~9 | | |
| Propylene glycol(PG) | 24 | 32~42 | | 10 | 55 | 47 | 52 | | | 25~55 | | |
| Stearyl Alcohol | 16 | — | — | — | — | — | — | — | — | — | — | — |
| Propylene glycol stearate | — | — | — | — | — | — | — | — | — | — | — | — |
| Phospholipon 90H | — | 3 | 3 | 3 | 4 | 3 | 3 | 4 | 4 | 4 | 4 | 4 |
| Ethanol | — | — | — | — | — | — | — | — | — | — | 10.5 | 10.5 |
| Aluminum starch octenyl-succinate | 11 | 11 | 11 | — | — | — | — | — | — | — | — | — |
| Appearance | Little dry cream | Cream | Cream | Liquid | Ointment | Oily cream | Very oily cream | Cream | Cream | Cream | Cream | Cream |
| Approximate solubility (%) | — | — | — | — | <1.3% | <3% | — | <0.1% | <0.3% | <0.7% | <2.3% | <2.5% |

As shown in Table 5, it was found the composition ratios of 2-2, 2-3, 2-8, 2-9, 2-10, 2-11, and 2-12 provide suitable cream type formulation. From the aforementioned result, it was confirmed that the amount ratios of water, white petrolatum, white wax, and propylene glycol have critical significance in the aforementioned ranges.

3. Optimization Test of Cream Processing Method

A condition that satisfies the physical and chemical stability with a target drug concentration (1%) was screened based on the amount ratios discovered in the composition optimization test. For this purpose, the ingredients other than the solvents such as propylene glycol and water were mixed according to the amount ratios disclosed in Table 6 under 70° C., and then the remaining solvents were mixed at 70° C. and 800 rpm or less. The mixed cream composition was stirred at or less than 100 rpm and cooled to room temperature.

Physical stabilities were measured by checking with the naked eye whether or not phase separation occurred after leaving a sample for a certain period of time at a condition of 25° C., 30° C. or 40° C. This is a test to discover an optimized processing method for obtaining a cream formulation.

TABLE 6

| Ingredients (wt %) | samples | | | | | | | | | | | |
|---|---|---|---|---|---|---|---|---|---|---|---|---|
| | 3-1 | 3-2 | 3-3 | 3-4 | 3-5 | 3-6 | 3-7 | 3-8 | 3-9 | 3-10 | 3-11 | 3-12 |
| Zileuton | — | — | — | — | — | — | — | — | — | — | — | — |
| Water | | | | 10~12 | | | | | | 17~21 | | |
| White petrolatum | | | | 18~20 | | | | | | 17~21 | | |
| White wax | 6 | 6 | 6 | 6 | 6 | 6 | 6 | 6 | 6 | 6 | 6 | 6 |
| Propylene glycol(PG) | 51 | 51 | 53 | 55 | 55 | 51 | 54 | 51 | 48 | 52 | 54 | 56 |
| Phospholipon 90H | 4 | 4 | 4 | 4 | 4 | 5 | 5 | 4 | 4 | 4 | 4 | 4 |
| Ethanol | | | | 4.5~9 | | | | | — | — | — | — |
| Stirring time(min) | 20 | 20 | 20 | 20 | 20 | 20 | 20 | 20 | 20 | 20 | 20 | 20 |
| Shape | Cream | Cream | Cream | Cream | Cream | Cream | Cream | Cream | Cream | Cream | Cream | Cream |
| Approximate solubility (%) | <2.1% | <1.8% | <2.7% | <2.7% | <2.3% | <2.1% | <2.1% | <2.1% | <1.3% | <1.5% | <1.7% | <2.1% |
| Physical stability at 25° C. | Bad | Bad | Bad | Bad | Bad | Bad | Bad | Bad | Good | Good | Good | Good |

As disclosed in Table 6, it was found that the formulation conditions of 3-9, 3-10, 3-11, and 3-12 provide excellent physical stability at 25° C. so as to dissolve active pharmaceutical ingredient 1% or more. Furthermore, the aforementioned cream formulations do not comprise ethanol, and this is because ethanol deteriorates physical stability.

Next, as a test for optimizing the processing method for cream type formulation, in order to find out whether the stirring time affects the shape of the cream, stirring times of 5 minutes, 30 minutes and 60 minutes were applied and then observed. As a result, as illustrated in Table 7 below, the stirring time of 30 minutes was confirmed as the optimized condition.

TABLE 7

| | samples | | |
|---|---|---|---|
| Ingredients(wt %) | 3-13 | 3-14 | 3-15 |
| Zileuton | — | — | — |
| Water | | 10~26 | |
| White petrolatum | | 17~29 | |
| White wax | 6 | 6 | 6 |
| Propylene glycol(PG) | | 35~56 | |
| Phospholipon 90H | 4 | 4 | 4 |
| Ethanol | 6.5 | — | — |
| Total sum of ingredients | 100 | 100 | 100 |
| Stirring time(min) | 5 | 30 | 60 |
| Appearance | Liquid like Cream | Cream | Cream |
| Approximate solubility (%) | — | 0.3% | <1.3% |
| Physical stability at 30° C. | | Good | |

4. Optimization Test of Solvent

It was determined that using an excessive amount of propylene glycol to adjust to 1% of drug concentration has a negative effect on the physical stability of the composition, and thus a composition ratio of high stability with a lower drug concentration was sought for.

Therefore, in order to improve the physical stability of the composition after increasing the scale of sample, a cream type formulation with a reduced loading amount of drugs was prepared. For this purpose, formulation 3-14 was selected, and based on this cream type composition, the amount of drug loading was raised up to 1%, and then a solvent capable of obtaining chemical stability while retaining physical stability was screened.

The aforementioned screening test was conducted by mixing ingredients other than the solvents such as propylene glycol, water and the like at 70° C. in accordance with the composition ratio disclosed in Table 8 below, and then mixing the remaining solvents according to the composition ratio of Table 8 under a stirring condition of 800 rpm or less for 30 minutes at 70° C. The mixed composition was stirred at or less than 100 rpm and cooled to room temperature.

The chemical stability was evaluated by measuring changes in TRS % through LC analysis after leaving a sample for a certain period of time under a temperature of 25° C. or 40° C.

TABLE 8

| Ingredients (wt %) | samples | | | | | | | | | |
|---|---|---|---|---|---|---|---|---|---|---|
| | N-methyl pyrrolidone (NMP) | | | Capyrol 90 | | | Benzyl alcohol | | | |
| | 4-1 | 4-2 | 4-3 | 4-4 | 4-5 | 4-6 | 4-7 | 4-8 | 4-9 | 4-10 |
| Zileuton | — | — | — | — | — | — | — | — | — | — |
| Water | | 24~26 | | | 20~24 | | | 37~41 | | |
| White petrolatum | | 29~33 | | | 29~33 | | | 38~42 | | |
| White wax | 6 | 6 | 6 | 12~24 | | | 6 | | | |

TABLE 8-continued

| Ingredients (wt %) | N-methyl pyrrolidone (NMP) | | | Capyrol 90 | | | Benzyl alcohol | | | |
|---|---|---|---|---|---|---|---|---|---|---|
| | 4-1 | 4-2 | 4-3 | 4-4 | 4-5 | 4-6 | 4-7 | 4-8 | 4-9 | 4-10 |
| Propylene glycol(PG) | 24 | 24 | 24 | — | — | — | — | — | — | — |
| Stearyl Alcohol | — | — | — | — | — | — | 4 | — | — | — |
| Propylene glycol stearate | — | — | — | — | — | — | — | 4 | — | — |
| Phospholipon 90H | 4 | 4 | 4 | 4 | 4 | 4 | — | — | 4 | 4 |
| Ethanol | — | — | — | — | — | — | — | — | — | — |
| Aluminum starch octenyl-succinate | — | — | — | — | — | — | — | — | — | — |
| N-methyl pyrrolidone (NMP) | 10 | 10 | 8 | — | — | — | — | — | — | — |
| Benzyl alcohol | — | — | — | — | — | — | 14 | 14 | 10 | 10 |
| Capryol 90 | — | — | — | 28 | 28 | 28 | — | — | — | — |
| Dimethyl sulfoxide | — | — | — | — | — | — | — | — | — | — |
| Stirring time (min) | 30 | 30 | 30 | 30 | 30 | 30 | 30 | 30 | 30 | 30 |
| Appearance | Liquid | Liquid | Cream | Cream | Cream | Cream | Cream | Cream | Cream | Cream |
| Approximate solubility (%) | 1% | 1% | 0.8% | 0.8% | 0.8% | 0.8% | | | | |
| Physical stability at 30° C. | | | Bad | | | | | | | |
| Physical stability at 40° C. | | | | Bad | Bad | Bad | Bad | Bad | Bad | Bad |

As illustrated in Table 8, NMP and benzyl alcohol were screened as solvents, but both showed bad physical stability with phase separation. Furthermore, capryol 90 was screened as a solvent, but all showed bad physical stability due to phase separation.

Consequently, the processing method was changed from 3-14 condition, and an amount of drug loading was increased to 1%, and thereby a cream type composition that satisfies both the target drug concentration and physical stability was discovered. However, regarding the chemical stability, a significant TRS % change was observed after 3 weeks under a temperature condition of 40° C.

5. Test for Confirming an Improvement in Stability of the Composition by Use of a pH Buffer Solution as Solvent In order to confirm the effect of a pH buffer solution on the chemical stability of the composition, the compositions were prepared by mixing ingredients other than the solvents at 70° C. in accordance with the composition ratios disclosed in Table 9 below, and then mixing the remaining solvents according to the composition ratios of Table 9 under a stirring condition of 800 rpm or less for 30 minutes at 70° C. The mixed compositions were stirred at or less than 100 rpm and cooled to room temperature.

The chemical stability was evaluated by measuring changes in pH, quantitative analysis of degradants of zileuton by HPLC, and TRS % through LC analysis after leaving a sample for a certain period of time under the storage condition of a room temperature of 25° C.(RT) and 40° C.

TABLE 9

| | samples | |
|---|---|---|
| Ingredients(wt %) | 5-1 | 5-2 |
| Zileuton | 1.0 | 1.0 |
| pH buffer solution* | — | 32 |
| Water | 32 | — |
| White petrolatum | 36-40 | |
| White wax | 4-8 | |
| Propylene glycol | 16-22 | |
| Phospholipon 90H | 2-6 | |
| Propylparaben | 0.005-0.04 | |
| Total sum of ingredients | 100 | |
| Appearance | Cream | Cream |

*pH buffer solution at pH 4, 5 and 6 with various concentration

As illustrated in FIG. 1, pH changes of the pH buffered creams at pH 4 and pH 5 were lowered in comparison with the non-buffered cream under accelerated condition (40° C.). It is noted that the pH buffered cream with a pH buffer solution of pH 4 can be controlled between pH 4.5 to 5 at which the generation of hydrolytic degradants of zileuton, i.e. impurities, are mostly suppressed, even at 40° C. when 10 mM to 100 mM pH buffer solutions were used, while the pH of the non-buffered control sample was changed to ~pH 7.

Furthermore, as illustrated in Table 10 below, the changes of TRS (total related substances) of the non-buffered control composition was increased up to 9.96% at 40° C. for 2 months, while the changes of TRS of the buffered composition with 25 mM pH buffer solution of pH 4 was only increased up to 2.74% in the same condition.

TABLE 10

|  | *Initial non-buffered | 40° C./3 Weeks | | | 40° C./2 months | | |
| --- | --- | --- | --- | --- | --- | --- | --- |
|  |  | non-buffered | pH 4 10 mM | pH 4 25 mM | non-buffered | pH 4 10 mM | pH 4 25 mM |
| Total related substance | 0.23% | 2.18% | 1.60% | 1.52% | 10.19% | 3.29% | 2.97% |
| % Change of TRS | — | 1.95% | 1.37% | 1.29% | 9.96% | 3.06% | 2.74% |

*Initial: day of formulation

6. Optimization Test of the Amount of Ingredients

Furthermore, as Illustrated in Table 11 Below, a Test for Determining a Critical Amount range of ingredients was conducted after selecting an ingredients and an approximate composition ratio that could satisfy criteria as a topical cream.

TABLE 11

| | | samples | |
| --- | --- | --- | --- |
| Ingredients (wt %) | Criteria | 6-1 | 6-2 |
| Zileuton | — | — | — |
| Water | 30~40 | 32 | 32 |
| White petrolatum | 36~40 | 33 | 38 |
| White wax | 4~8 | 6 | 6 |
| Propylene glycol | 16~22 | 25 | 19 |
| Phospholipon 90H | 2~6 | 4 | 4 |
| Appearance | Cream | Cream | Cream |
| Physical stability for 4 weeks under 40° C. | Stable | Phase separation observed at the 4th week | Stable |

As shown in Table 11, as in the formulation 6-1, when the amount ratio of white petrolatum and propylene glycol are 33 and 25, respectively, it was observed by naked eyes that the physical stability was deteriorated due to separation of oil phase and water phase starting from the 4th week.

Table 12 below shows candidate formulations according to the test result.

TABLE 12

|  | Candidate formulations samples | |
| --- | --- | --- |
| Ingredients (wt %) | 6-3 | 6-4 |
| Zileuton | 1 | 1 |
| Water | 32 | 26 |
| White petrolatum | 32 | 29 |
| White wax | 6 | 6 |
| Propylene glycol (PG) | 25 | 34 |
| Phospholipon 90H | 4 | 4 |
| Total sum of ingredients | 100 | 100 |

TABLE 12-continued

|  | Candidate formulations samples | |
| --- | --- | --- |
| Ingredients (wt %) | 6-3 | 6-4 |
| Stirring time (min) | 30 | 30 |
| Appearance | Cream | Cream |
| Approximate solubility (%) | 1% | 1% |
| Physical stability at 40° C. | Good | Good |

TABLE 12-continued

|  | Candidate formulations samples | |
| --- | --- | --- |
| Ingredients (wt %) | 6-3 | 6-4 |
| Chemical stability at 40° C. (TRS %) | 6.65% of changes for 3 weeks | 9.79% of changes for 3 weeks |

As shown in Table 13, the formulations 6-3 and 6-4 satisfied conditions required for development up to clinical phase 2. Further, in order to develop the final formulation, an experiment for developing a new composition ratio and processing method was additionally conducted while measuring the chemical stability under 30° C. acceleration condition of 062-1.

Accordingly, as shown in Table 13 below, the amount of propylene glycol was optimized, and propylene paraben was added as a preservative. As a result, the cream formulations 6-5 and 6-6 of the composition ratios of Table 13 satisfied chemical/physical stabilities under 30° C. acceleration condition.

TABLE 13

|  | samples | |
| --- | --- | --- |
| Ingredients(wt %) | 6-5 | 6-6 |
| zileuton | 0.1 | 1 |
| Water | 30-34 | 30-34 |
| White Petrolatum | 36-40 | 36-40 |
| White wax | 4-8 | 4-8 |
| Propylene glycol | 16-22 | 16-22 |
| Phospholipon 90H | 2-6 | 2-6 |
| Preservative (Propylparaben) | 0.05-0.4 | 0.05-0.4 |
| Total sum of ingredients | 100 | 100 |
| Stirring time (min) | 30 | 30 |
| Appearance | Cream | Cream |
| Physical stability | Good for 4 weeks | Good for 4 weeks |
| Chemical stability (TRS %) | 1.4% of changes for 4 weeks at 30° C. | 1.4% of changes for 4 weeks at 30° C. |

On the other hand, it was confirmed that the cream formulations of the comparative examples having composition ratios of Table 14 below do not exhibit good chemical/physical stabilities under 30° C. acceleration condition in the target drug concentration range which can provide efficacious pharmaceutical activity.

TABLE 14

| Ingredients(wt %) | samples | |
| --- | --- | --- |
| | 6-7 | 6-8 |
| zileuton | 0.7 | 0.7 |
| Water | 24 | 22 |
| White Petrolatum | 25 | 27 |
| White wax | 3 | 3 |
| Propylene glycol | 46 | 46 |
| Phospholipon 90H | 1 | 1 |
| Preservative (Propylparaben) | 0.02 | 0.02 |
| Stirring time (min) | 30 | 30 |
| Appearance | Cream | Cream |
| Physical stability | Phase separation observed at 30° C. | Phase separation observed at 30° C. |

Experiment 1 Evidence of Concept Research Using Formulation 089

An in vivo test was conducted to identify whether or not the formulation 6-6 of the above example shows medical effects when administered to skin in a generally used mouse atopic dermatitis animal model. For this purpose, BALB/c mice were divided into 4 groups, each consisting of 10 mice. The groups were divided into a vehicle (acetone), positive control group (dexamethasone 0.05 mg/ear; Dex), and zileuton groups (Formulation 5-6). And the zileuton groups were divided into cases where acetone (1 mg/ear) and the cream formulation of 6-6 (0.2 mg/ear and 0.02 mg/ear) were used, respectively.

Figure 2:
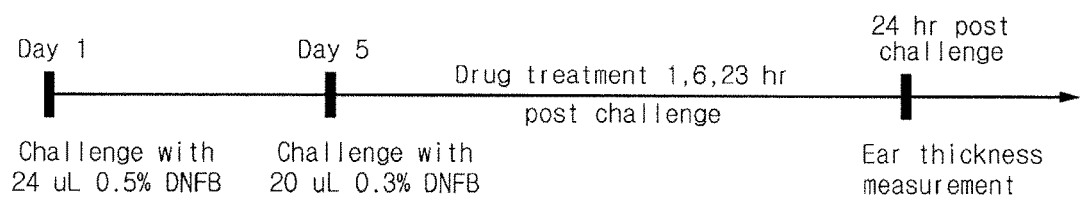
FIG. 2 is a schematic diagram illustrating results of a test conducted to verify medical effects of the pharmaceutical composition according to the present invention by applying the same to an atopic mouse model.

As illustrated in FIG. 2, on day 0 and day 1, 25 µl of 0.5% DNFB (dinitrofluorobenzene) solution was applied once on ears of all groups to cause inflammation. Then, on day 5, 20 µl of 0.3% DNFB was applied once again to cause inflammation in the ears. Then, dexamethasone and zileuton dissolved in acetone vehicle were applied to the ears at 1 hour, 6 hours, and 23 hours after the stimulation on day 5. Thicknesses of the ears were measured at 24 hours after the stimulation on day 5, and then ear tissues were taken for histopathological observation.

Figure 3:
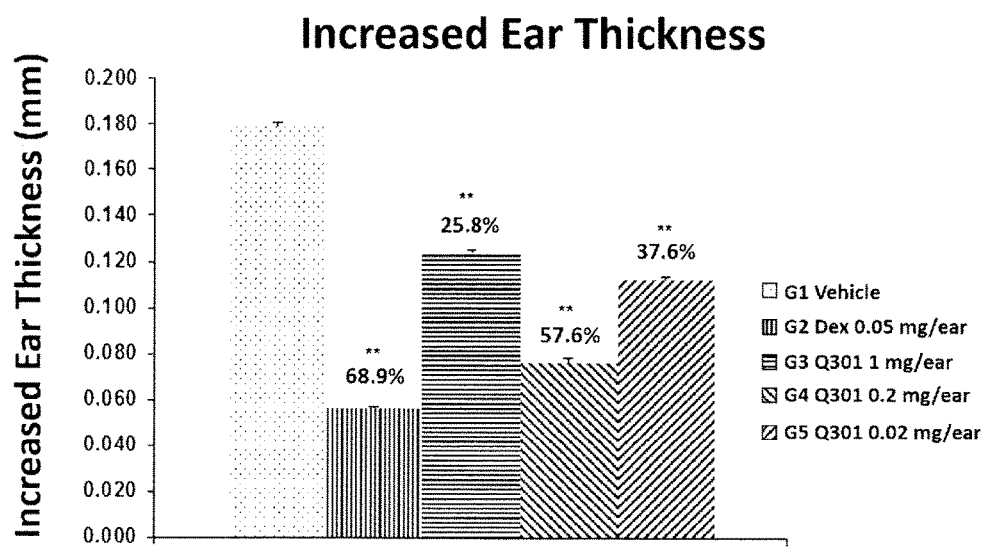
FIG. 3 is a graph showing thicknesses of a mouse's ear measured after topically applying the pharmaceutical composition according to the present invention to an atopic mouse model.

As illustrated in FIG. 3, in the group where the formulation 6-6 was used, zileuton (API: Active Pharmaceutical Ingredient) was effectively delivered to the skin, thereby effectively inhibiting increase of ear thickness caused by inflammation and edema compared to groups where acetone was used.

Through histopathological observation, excellent anti-inflammation function of zileuton was observed.

TABLE 15

| | Test model | | | | | | |
| --- | --- | --- | --- | --- | --- | --- | --- |
| | BALB/c mouse, female 6~8 weeks of age (17~20 g) | | | | | | |
| | Dosing | | | | | | |
| Group | Drug (formulation) | No. | Route | Concentration (mg/mL or %) | mL or mg/ear | API mg/ear | Regimen (Time) |
| 1 | Vehicle (Acetone) | 10 | Topical | N/A | 0.02 mL | N/A | 1, 6, 23 |
| 2 | Dex (Acetone) | 10 | Topical | 2.5 mg/mL | 0.02 mL | 0.05 | 1, 6, 23 |
| 3 | Zileuton (Acetone) | 10 | Topical | 50 mg/mL | 0.02 mL | 1 | 1, 6, 23 |
| 4 | Zileuton (formulation 5-6) | 10 | Topical | 1 wt % | 20 mg | 0.2 | 1, 6, 23 |
| 5 | zileuton (formulation 5-6 except of zileuton 0.1 wt %) | 10 | Topical | 0.1 wt % | 20 mg | 0.02 | 1, 6, 23 |
| Measure | Weight Ear thickness Histopathological observation (edema, inflammation, crust formation) | | | | | | |

Experiment 2 PK Research Test Using Minipigs

It is necessary to find out from the Experiment 1 whether or not medical effects by absorption to an entirety of body are included. In order to identify the skin absorption and systemic exposure level of the final formulation, minipigs having skin structures most similar to those of humans may be used. Therefore, skin PK was observed in minipigs having the most similar skin structures as humans using the formulation 6-6 which is for the clinical formulation derived in the process of developing the cream formulation.

For this purpose, 20 mg of zileuton (API: Active Pharmaceutical Ingredient) was applied to 100 cm$^2$ of skin using the formulation 6-6. After applying the formulation 6-6, concentration of zileuton in plasma was measured 0.25, 0.5, 1, 1.5, 2, 3, 4, 6, and 8 hours afterwards. After applying the formulation 6-6, zileuton concentration in the skin was measured 1 and 8 hours afterwards. For the measurement of zileuton concentration in the skin, the skin was separated into surface, subcutaneous, dermas, and epidermis layers. The subcutaneous layer was separated using the tape stripping method, and the measurements of zileuton concentrations were conducted for different depths of strip 1, strip 2-5, strip 6-12, and strip 13-24. Test conditions are as illustrated in Tables 16 and 17.

TABLE 16

| Group | Number of Bamma pigs (#/Gender) | Test drug | Treatment | | | | Type of specimen obtained |
|---|---|---|---|---|---|---|---|
| | | | Dose (mg/cm$^2$) | Concentration (mg API/g cream) | Vehicle | Route | |
| 1 | 6 females | Zileuton (Q301) | 0.2(API) | 10 | 6-6 Formulation | Topical administration | Plasma, skin |

Test article storage: Desiccated at 4° C.
Comments: Animals of body weights of 15~20 kg were used, and administration area was 10 cm × 10 cm
Overnight Fast of Animals: None

TABLE 17

| Group | Administration route | Animal ID | Sampling and administration schedule (time) | | | | | | | | | | |
|---|---|---|---|---|---|---|---|---|---|---|---|---|---|
| | | | −0.5 | 0 | 0.25 | 0.5 | 1 | 1.5 | 2 | 3 | 4 | 6 | 8 |
| 1 | Topical | 1~3 | P | D | P | 0 | P + S | — | — | — | — | — | — |
| | | 4~6 | P | D | — | P | — | P | P | P | P | P | P + S |

Figure 4:
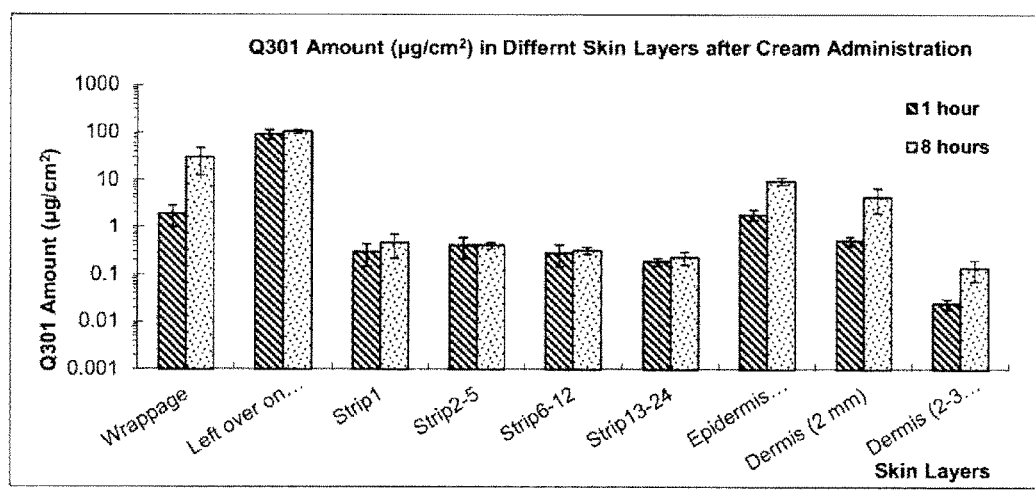

P: Collect blood and separate plasma
D: Administer drug to animals at determined time
P + S: Collect blood and skin, and separate plasma from blood. Extract corneum layer before obtaining skin sample. Separate dermas and epidermis layers from skin.
Anticoagulant: K2-EDTA As illustrated in FIGS. 4 and 5, the formulation 6-6 showed effective skin absorption pattern, whereas it did not show any systemic exposure pattern in the minipigs. It can be seen that the cream formulation using propylene glycol effectively induces skin absorption, and minimizes body absorption, and is thus suitable as a future candidate formulation of zileuton for skin administration.

While this invention has been described in connection with what is presently considered to be preferable embodiments, it is to be understood that the present invention is intended to cover various changes, modifications and equivalent arrangements. It is obvious that the present invention may be practiced by appropriate modifications of the aforementioned embodiments. Therefore, the aforementioned embodiments do not limit the scope of the present invention which is determined by the claims.

INDUSTRIAL APPLICABILITY

The present invention is for providing a zileuton cream formulation for topical treatment of skin disease caused by leukotriene, and is an industrially applicable invention.

We claim:

1. A topical anti-inflammatory pharmaceutical composition, comprising zileuton, an aqueous solvent, an organic solvent, a thickening agent, and an emulsifier, wherein the composition comprises zileuton of about 0.05 to about 2 weight %; pH buffer solution of about 30 to about 34 weight %; white petrolatum of about 36 to about 40 weight %; white wax of about 4 to about 8 weight %; propylene glycol of about 16 to about 22 weight %; phospholipid of about 2 to about 6 weight %; and preservative of about 0.005 to about 0.04 weight %.

2. The composition according to claim 1, wherein the pH buffer solution has a pH of about 4 to about 5.

3. The composition according to claim 2, wherein the pH buffer solution is citrate buffer, acetate buffer or phthalate buffer.

4. The composition according to claim 1, wherein the phospholipid is phospholipon 90H.

5. The composition according to claim 1, wherein the preservative is at least one selected from a group consisting of methylparaben, ethylparaben, propylparaben, isobutylparaben, butyl paraben, 2-phenoxy ethanol, and 4-hydroxybenzoic acid.

6. The composition according to claim 1, wherein the composition comprises zileuton of about 0.1 to about 1 weight %; water or pH buffer solution of about 31 to about 33 weight %; white petrolatum of about 37 to about 39 weight %; white wax of about 5 to about 7 weight %; propylene glycol of about 18 to about 20 weight %; phospholipid of about 3 to about 5 weight %; and preservative of about 0.01 to about 0.03 weight %.

7. The composition according to claim 1, wherein the composition is formulated for topical application to human skin.

8. The composition according to claim 1, wherein zileuton is racemic zileuton.

9. A method for relieving or treating atopic dermatitis, acne, urticaria, psoriasis, eczema, a bullous skin disease, collagenoses, Sjogren-Larsson syndrome, or acne in skin lesions of mastocytosis, wherein said method comprises administering, to a subject in need of such relief or treatment, a composition of claim 1.

10. The method according to claim 9, wherein the composition is applied topically to human skin.

11. The composition according to claim 1, wherein the composition is a cream.

* * * * *